US006894502B2

United States Patent
Feng et al.

(10) Patent No.: US 6,894,502 B2
(45) Date of Patent: May 17, 2005

(54) PH SENSOR WITH INTERNAL SOLUTION GROUND

(75) Inventors: Chang-Dong Feng, Long Beach, CA (US); Joe N. Covey, Tustin, CA (US); Beth Meinhard Covey, Tustin, CA (US); Richard N. Baril, Huntington Beach, CA (US); Roland H. Koluvek, Orange, CA (US)

(73) Assignee: Rosemount Analytical Inc., Anaheim, CA (US)

(*) Notice: Subject to any disclaimer, the term of this patent is extended or adjusted under 35 U.S.C. 154(b) by 5 days.

(21) Appl. No.: 10/319,430

(22) Filed: Dec. 13, 2002

(65) Prior Publication Data

US 2003/0132755 A1 Jul. 17, 2003

Related U.S. Application Data

(60) Provisional application No. 60/340,413, filed on Dec. 14, 2001.

(51) Int. Cl.[7] .................. G01N 27/416; G01N 27/02
(52) U.S. Cl. ................... 324/438; 324/444; 324/446
(58) Field of Search ............... 324/438, 439, 324/446, 425, 444

(56) References Cited

U.S. PATENT DOCUMENTS

| 2,852,738 A | 9/1958 | Sherman ............. 324/54 |
| 3,360,719 A | 12/1967 | Saito et al. ............ 324/31 |
| 3,661,748 A | 5/1972 | Blackmer ............. 204/155 |

(Continued)

FOREIGN PATENT DOCUMENTS

| DE | 3239572 | 5/1983 |
| WO | WO 01/75430 A2 | 11/2001 |

OTHER PUBLICATIONS

Telli et al., "Study of a pH Sensor with MnO2 and Montmorillonite–based Solid–state Internal Reference", Solid State Ionics, North Holland Pub. Company, Amsterdam, NL, vol. 128, No. 1–4, pp. 255–259, Feb. 2000 (XP004190613).
Peters G, "A Reference Electrode with Free–Diffusion Liquid Junction for Electrochemical Measurements Under Changing Pressure Conditions", Analytical Chemistry, American Chemical Society, Columbus, US, vol. 69, No. 13, pp. 2362–2366, Jul. 1, 1997 (XP000696558).

*Primary Examiner*—N. Le
*Assistant Examiner*—John Teresinski
(74) *Attorney, Agent, or Firm*—Westman, Champlin & Kelly, P.A.

(57) ABSTRACT

The invention relates to an internal solution ground for primary use with a pH sensor, and preferably with a multi-sensing instrument monitoring a pH sensor and one or more additional secondary sensors having non-isolated circuits. In one aspect, a pH sensor assembly includes a pH electrode, a reference electrode, and an internal solution ground wire. The internal solution ground wire shares a liquid junction with the reference electrode but is protected by the reference fill solution. In one embodiment, the internal solution ground can be electrically isolated through a capacitor or, alternately, a capacitor and resistor in parallel.

12 Claims, 7 Drawing Sheets

U.S. PATENT DOCUMENTS

| | | | |
|---|---|---|---|
| 3,718,568 A | 2/1973 | Neuwelt | 201/195 P |
| 3,862,895 A | 1/1975 | King et al. | 204/195 R |
| 4,013,899 A | 3/1977 | Guicheteau | 307/235 F |
| 4,094,186 A | 6/1978 | Wessel | 73/1 G |
| 4,167,163 A | 9/1979 | Moder | 123/119 EC |
| 4,189,367 A | 2/1980 | Connery et al. | 204/195 |
| 4,218,746 A | 8/1980 | Koshiishi | 364/571 |
| 4,443,763 A | 4/1984 | Karsoner | 324/439 |
| 4,468,608 A | 8/1984 | Rolfe | 324/51 |
| 4,506,226 A * | 3/1985 | Luce et al. | 324/459 |
| 4,536,274 A | 8/1985 | Papadakis et al. | 204/433 |
| 4,546,441 A | 10/1985 | Burch | 364/482 |
| 4,568,444 A | 2/1986 | Nakamura et al. | 204/412 |
| 4,686,011 A | 8/1987 | Jäckle | 204/1 T |
| 4,777,444 A | 10/1988 | Beijk et al. | 324/438 |
| 4,822,456 A | 4/1989 | Bryan | 204/1 T |
| 4,829,253 A | 5/1989 | Koluvek | 324/438 |
| 4,998,068 A | 3/1991 | McKee, Jr. | |
| 5,046,028 A | 9/1991 | Bryan et al. | 364/550 |
| 5,059,908 A | 10/1991 | Mina | 324/444 |
| 5,268,852 A | 12/1993 | Forsythe et al. | 364/482 |
| 5,469,070 A | 11/1995 | Koluvek | 324/713 |
| 6,353,323 B1 * | 3/2002 | Fuggle | 324/438 |
| 6,419,809 B1 | 7/2002 | Suzuki et al. | 204/435 |

* cited by examiner

PH SENSOR WITH INTERNAL SOLUTION GROUND

CROSS REFERENCE TO RELATED APPLICATION

This application claims the benefit of U.S. Provisional Application No. 60/340,413 entitled, "INTERNAL SOLUTION GROUND" filed on Dec. 14, 2001, the content of which is incorporated herein by reference in its entirety.

BACKGROUND OF THE INVENTION

Galvanic cells that measure pH are well known in the prior art. Conventionally, pH sensors often consist of a measurement or pH electrode and reference electrode, each having a silver wire (Ag) with a silver chloride (AgCl) coating at its end. The pH electrode typically has an internal-filled chloride buffer in aqueous solution having a selected pH (chloride buffer) that is often a pH of about 7 and a pH sensitive glass surrounding the internal silver wire and chloride buffer. The reference electrode typically has a container with an internal-filled reference solution of potassium chloride in aqueous solution (reference solution).

The pH-sensitive glass bulb normally encloses and contacts the internal chloride buffer and is then placed in an external liquid sample or process stream to measure pH. The glass typically has two hydrated gel layers, one layer on the inside surface and another on the outside surface. The actual pH sensing is accomplished when a potential difference develops between the two hydrated gel layers. A hydrogen ion does not exist by itself in aqueous solution. It is associated with a water molecule to form a hydronium ion ($H_3O'$). The glass enclosed pH electrode develops a potential when hydronium ions get close enough to the glass bulb surface for hydrogen ions to jump and become associated with hydronium ions in an outer hydrated gel layer disposed on the glass bulb surface. This thin gel layer is essential for electrode response. The input to the pH measurement circuit in a pH sensor is the potential difference that develops between the eternal glass surface having potential $E_g$ that is exposed to the sample liquid and the internal glass surface having potential $E_r$ that is wetted by the chloride buffer having the selected pH. The potential difference that develops follows the Nernst equation. Assuming the chloride buffer has a temperature of 25° C. and a pH of 7 then the potential difference (which is conventionally also the input to the pH measurement circuit) is:

$$E_g - E_r = 0.1984\ (T+273.16)\ (7-\text{pH}).$$

The potential difference that develops is proportional to the deviation of the process pH from 7 pH at 25° C. If the pH of the process stream equals 7 then the potential difference measured will be zero.

However, all pH sensors have inherent sources of error. Error sources in sensors such as those described in U.S. Pat. Nos. 5,268,852 and 5,469,070 include glass impedance and liquid junction impedance. In general, solution ground is often a term used in instrumentation for glass bulb pH sensors. One potential use of a solution ground is ensuring that ground currents bypass the higher resistance path through the reference electrode to the instrument circuit ground. Another important use is in measuring glass and liquid junction impedance useful to estimate aging of the pH sensor as well as some physical conditions of the sensor. Increased sensor impedance from aging is associated with measurement errors as well as useful in predicting future sensor failure. Solution grounds are useful in sensor diagnostics because they can supply an extra electrode for injecting test currents into the sensor for diagnostic purposes.

In the prior art, a solution ground can be an external metal surface in contact with the liquid sample solution and electrically coupled to a circuit common of an instrument. These prior art solution grounds are external because they are external and normally attached to the sensor housing. Disadvantages of external solution grounds include relative high expense and difficulty in manufacturing. Also, the external solution grounds are usually made of metals such as stainless steel, platinum or titanium, which often do not establish stable potentials in the liquid sample.

Another disadvantage of external solution grounds is that they can leak voltage into the liquid sample in which pH is being measured. The leaked voltage can lead to ground loop currents, especially through the reference electrode. Ground loops can lead to damage in the reference electrode resulting in erroneous readings, calibration errors and shortened sensor life.

Finally, when a multi-sensing instrument monitors a pH sensor and one or more secondary sensors in a single sample solution, other ground loop problems and complications can result. Ground loops are especially a concern when pH sensor circuitry and secondary sensor circuitry are not isolated within the instrument. Ground loop problems are especially evident when an instrument monitors both a pH sensor and a conductivity sensor having non-isolated circuits within the multi-sensing instrument.

There exists a need for a solution ground for primary use with a pH sensor that overcomes one, some or all of the disadvantages of prior art solution grounds.

SUMMARY OF THE INVENTION

The invention relates to an internal solution ground for primary use with a pH sensor, and preferably with a multi-sensing instrument monitoring a pH sensor and one or more additional secondary sensors having non-isolated circuits. In one aspect, a pH sensor assembly includes a pH electrode, a reference electrode, and an internal solution ground wire. The internal solution ground wire shares a liquid junction with the reference electrode but is protected by the reference fill solution. In one embodiment, the internal solution ground can be electrically isolated through a capacitor or, alternately, a capacitor and resistor in parallel.

DETAILED DESCRIPTION OF THE ILLUSTRATIVE EMBODIMENTS

Conventional pH Sensor

Figure 1:
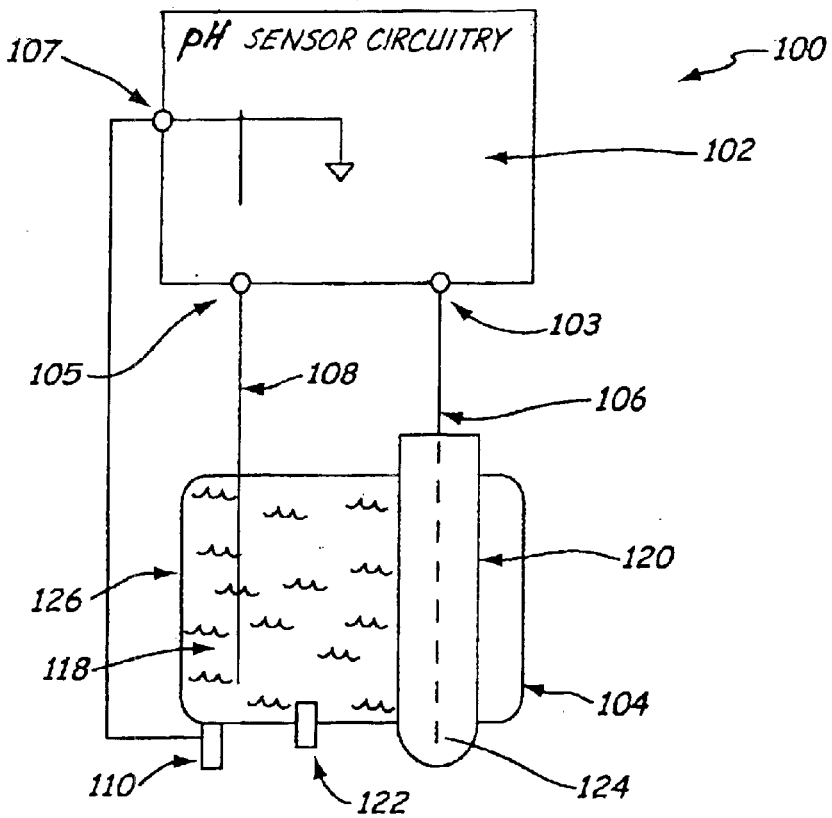
FIG. 1 illustrates diagrammatic view of a prior art pH sensor having an external solution ground.

FIG. 1 illustrates prior art pH sensor assembly 100 comprising circuitry 102 electrically coupled to well-known pH sensing probe 104 having pH electrode 106 and reference electrode 108. Conventionally, pH electrode 106 and reference electrode 108 each have a silver (Ag) wire coated with silver chloride (AgCl) at the end in contact with solution. Other pH and reference electrode materials, such as platinum, can be used.

The pH electrode 106 typically includes glass bulb 120 made of pH sensitive glass with an internal-filled aqueous chloride buffer solution 124 having a selected pH, e.g. approximately 7 (chloride buffer). Other buffer solutions can be used. Probe 104 further includes container 126 filled with reference solution 118 in contact with liquid junction 122 extending through to the outside surface of container 126. Container 126 is adaptable to be positioned in a liquid sample (not shown) for which pH is measured. Reference solution 118 can include aqueous potassium chloride solution (KCl) but other reference solutions can be used.

As discussed in the background section above, pH is measured when probe 104 is placed in a liquid sample (not shown) resulting in a potential difference $E_g - E_r$ developing between glass bulb 120 and reference electrode 108. Circuitry 102 includes terminal 103 and terminal 105. Terminal 103 is electrically connected to pH electrode 106 and has a voltage $V_g$. Terminal 105 is electrically connected to reference electrode 108 and has a voltage $V_r$.

To measure pH or perform diagnostics, alternating current can be injected across terminals 103 and 107 and terminals 105 and 107 using external solution ground 110 as common in both positive and negative directions. The potential difference $V_g - V_r$ that develops between terminal 103 and terminal 105 is associated with the pH of the sample liquid (not shown) and can be converted to a usable pH measurement by circuitry 102.

Disadvantages to External Solution Ground pH Measurement Errors

Figure 2:
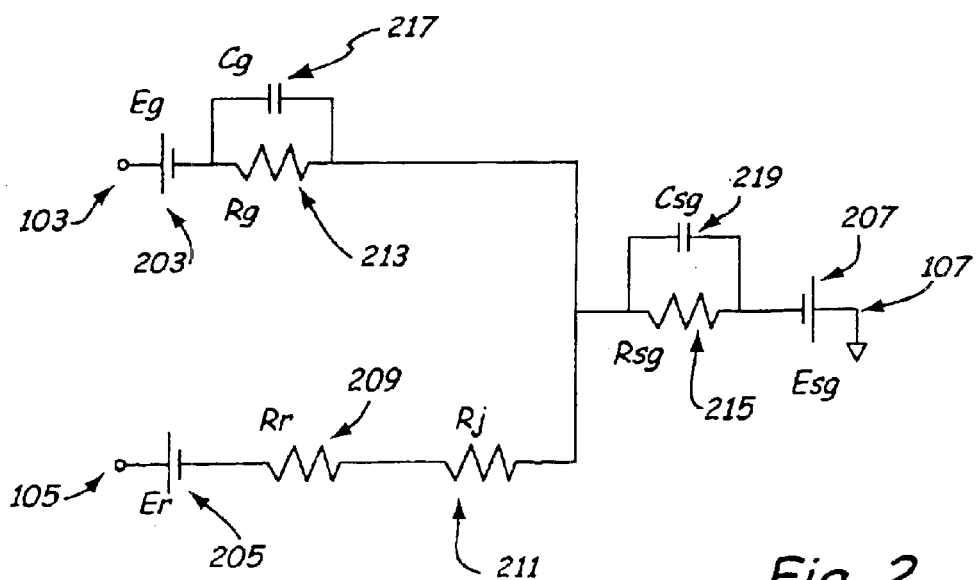
FIG. 2 illustrates a partial equivalent circuit of the pH sensor of FIG. 1.

In the prior art, solution ground 110 is used for both pH measurement and for sensor diagnostics. One disadvantage of external solution ground 110 is that it can lead to additional error in pH measurement due to ground loops. With a conventional pH sensor having external solution ground 110, a series of equations can be developed using principles of equivalent circuits and Ohm's Law. FIG. 2 illustrates a partial equivalent circuit for a pH sensor 100 having external solution ground 110. The equations are as follows:

$$V_r^+ = E_r + E_{sg} - i_r \frac{t_{1/2}}{C_{sg}} + i_g \frac{t_{1/2}}{C_{sg}} + i_r \left( R_j + R_r + \frac{t}{C_{sg}} \right) \quad \text{Eq. 1}$$

$$V_g^- = E_g + E_{sg} + i_r \frac{t_{1/2}}{C_{sg}} + i_g \frac{t_{1/2}}{C_{sg}} - i_g \left( \frac{1}{\frac{1}{R_g} + \frac{C_g}{t}} + \frac{t}{C_{sg}} \right) \quad \text{Eq. 2}$$

$$V_r^- = E_r + E_{sg} + i_r \frac{t_{1/2}}{C_{sg}} - i_g \frac{t_{1/2}}{C_{sg}} - i_r \left( R_j + R_r + \frac{t}{C_{sg}} \right) \quad \text{Eq. 3}$$

$$V_g^+ = E_g + E_{sg} - i_r \frac{t_{1/2}}{C_{sg}} - i_g \frac{t_{1/2}}{C_{sg}} + i_g \left( \frac{1}{\frac{1}{R_g} + \frac{C_g}{t}} + \frac{t}{C_{sg}} \right) \quad \text{Eq. 4}$$

where $V_r^+$ and $V_g^+$ are the voltage at reference electrode terminal 105 and pH electrode terminal 103, respectively, during positive current injection; $V_r^-$ and $V_g^-$ are the voltages at terminal 105 and terminal 103, respectively during negative current injection; $E_r$ 205 is the potential at reference electrode 108, $E_{sg}$ 207 is the potential at the metal surface of the solution ground 110 in liquid sample (not shown) and $E_g$ 203 is the potential at glass bulb 120; and t is time and $t_{1/2}$ is half of the time duration of the current injection.

The value of all the resister and capacitor components can be measured and known. In one embodiment, the time t is 100 mS, $R_r$ 209 is 2000 ohms, $R_j$ 211 is 500 ohms, $R_g$ 213 is 80 Mohms, $R_{sg}$ 215 is greater than 10 Mohms, $C_g$ 217 is 2.00E-10F, $C_{sg}$ 219 is 6.00E-06F where $R_r$ 209 is the internal resistance of reference electrode 118, $R_j$ 211 is the resistance of the liquid junction 122, $R_g$ 213 is the resistance of the pH sensing glass 120, $R_{sg}$ 215 is the charge transfer resistance of external solution ground 110, $C_g$ 217 is the capacitance across pH sensing glass 120, and $C_{sg}$ 219 is the double layer capacitance of external solution ground 110.

Figure 3:
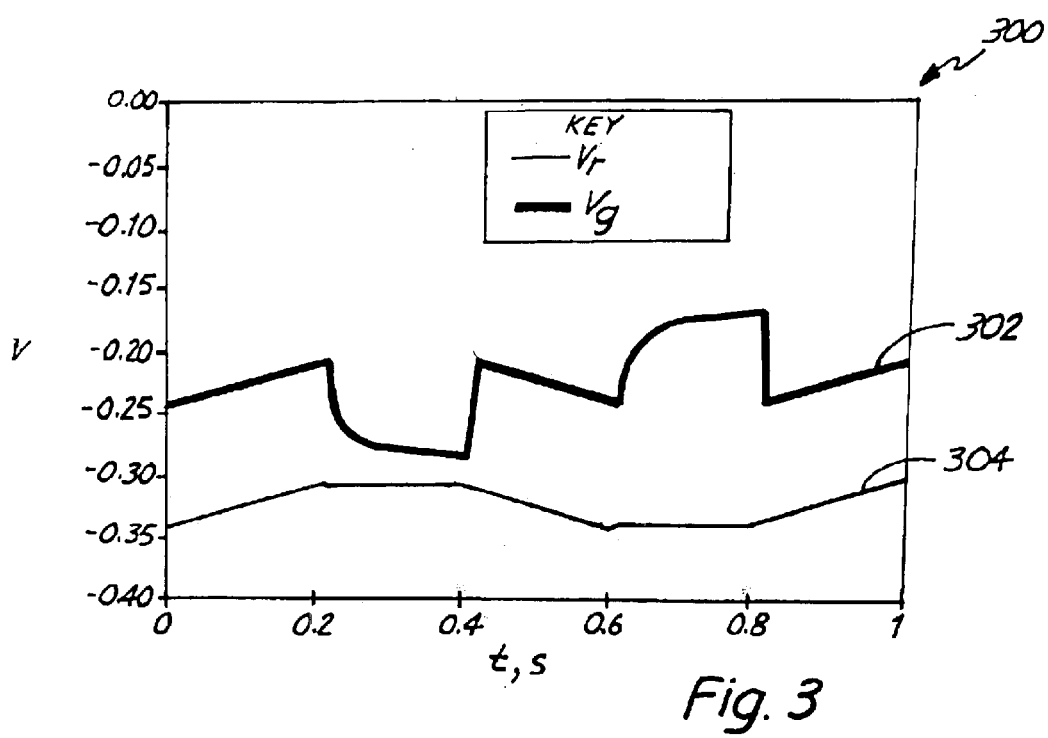
FIG. 3 illustrates a simulation graph for voltages across pH electrode and reference electrode of prior art pH sensors with external solution ground.
Figure 4:
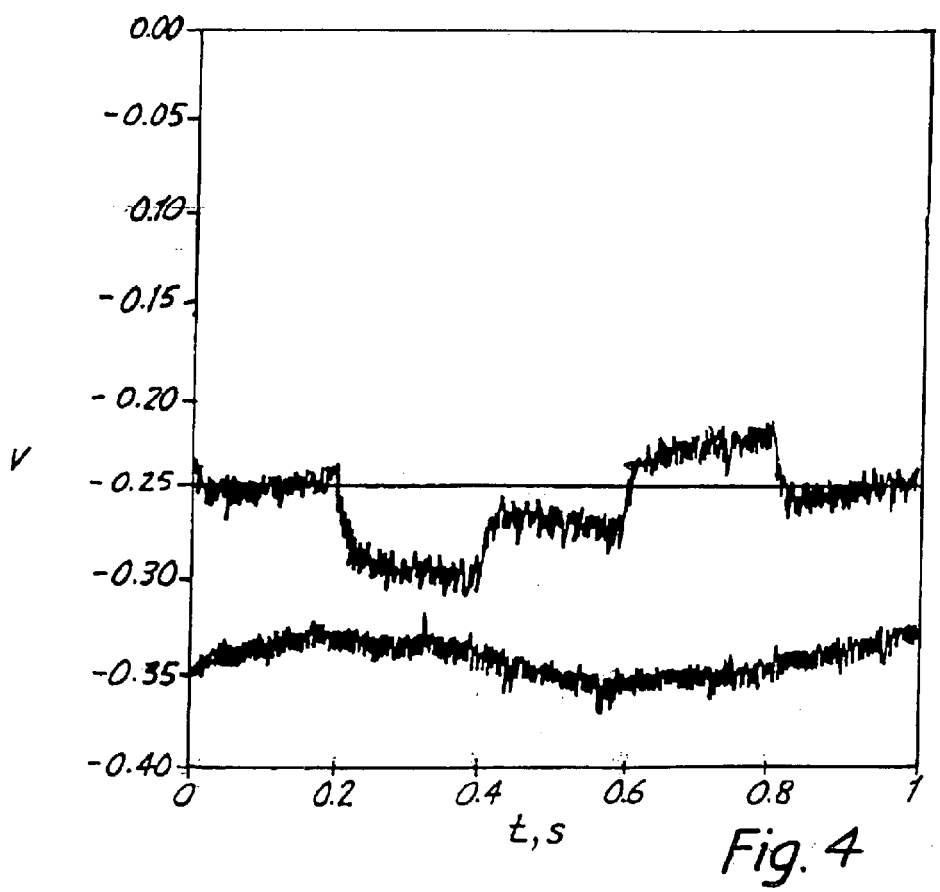
FIG. 4 illustrates oscilloscope results of voltages across pH electrode and reference electrode of prior art pH sensor with external solution ground with undesirable ramping.

By using these component values and by assuming $i_r$=1 µA and $i_g$=1 mA, graph 300 illustrates results of a computer-generated simulation, where the top plot 302 indicates voltage $V_g$ at terminal 103 and bottom plot 304 indicates voltage $V_r$ at terminal 105. Oscilloscope results of an actual pH sensor 100 using a platinum external solution ground 110 undergoing current injection for pH measurement are shown in FIG. 4. The oscilloscope graph shown in FIG. 4 clearly confirms the simulation results illustrated in FIG. 3. There is obvious undesirable ramping shown in FIG. 4.

Actual pH sensor measurement is associated with the potential difference $E_g - E_r$ at the glass bulb 120 and reference electrode 108. Circuitry 102 samples $V_r$ and $V_g$ at the end of both positive and negative current injection or $V_r^+$, $V_r^-$, $V_g^+$, and $V_g^-$. By adding equations 1 and 3 together and assuming that $V_r$=$(V_r^+ + V_r^-)/2$, then $V_r$=$E_r + E_{sg}$. Similarly by adding equations 2 and 4 together and assuming $V_r$=$(V_g^+ + V_g^-)/2$, then $V_g$=$E_g + E_{sg}$. By subtracting the equations for $V_r$ from $V_g$, then $V_g - V_r$=$E_g - E_r$. It is again noted that the pure potential difference signal needed for pH measurement is $E_g - E_r$.

However, for accurate pH readings the following conditions are present:

1. The instrument samples the voltages ($V_g^+$, $V_g^-$, $V_r^+$, $V_r^-$) for both positive and negative current injection at the same time duration of each current injection.
2. The absolute values of the positive and negative injected current i are the same.
3. All the resister components remain constant during both positive and negative current injections.

4. All capacitor components remain constant during both positive and negative current injections.

5. All voltage sources remain constant during both and negative current injections.

Conditions 1 and 2 have been found to be readily achievable by careful circuit design. However conditions 3, 4 and 5 have been found to be achievable only if all the components in the pH sensor are well-defined values. Generally, the potential $E_{sg}$ and double layer capacitance $C_{sg}$ components of the external solution ground 110 are not well-defined and can vary thereby causing error in pH measurement.

Much of the pH measurement error of the pH sensor shown in FIG. 1 is due to solution ground 110 being external to container 126 in direct contact with liquid sample (not shown). An external solution ground 110 is generally made of a chemical-resistant material such as platinum, titanium, or stainless steel. These metals do not reliably establish a stable potential $E_{sg}$ during pH measurement indicated by reference numeral 207 in FIG. 2. Therefore, external solution ground potential $E_{sg}$ and double layer capacitor components $C_{sg}$ indicated by reference numeral 219 in FIG. 2 will change depending on the magnitude and direction of the injected current as well as the liquid sample itself. The varying $E_{sg}$ leads to additional error in pH measurement for pH sensor 100 having an external solution ground 110.

Diagnostics

An external solution ground 110 also leads to error in measuring sensor impedance during diagnostics, especially measurements for glass impedance and liquid junction impedance. As sensors age, these impedance sources tend to increase. According to U.S. Pat. Nos. 5,268,852 and 5,469,070, hereby incorporated by reference, various protocols exist for performing sensor diagnostics by measuring various sources of sensor impedance. Commonly, alternating current is injected into both reference electrode 108 and pH electrode 106 using external solution ground 110 as common. By measuring potential differences that develop in response to the injected alternating current, the condition of the pH sensor can be reasonably determined for both maintenance purposes and to predict future sensor failure.

However, there are more obvious sources of error when performing diagnostics for glass bulb impedance and liquid junction impedance. Again, referring to equations 1 through 4 above which employ principles of equivalent circuits and Ohm's Law, when assuming that the measured glass impedance $$R_m = \frac{V_g^+ + V_g^-}{2i_g}$$

then equations 2 and 4 can be simplified to:

$$R_m = \left(\frac{i_r}{i_g}\right)\left(\frac{t_{1/2}}{C_{sg}}\right) - \frac{t_{1/2}}{C_{sg}} + \frac{1}{\frac{1}{R_g} + \frac{C_g}{t}} \quad \text{Eq. 5}$$

Further, since $$\frac{1}{R_g}$$

is significantly larger than $$\frac{C_g}{t} \text{ and } \frac{C_{sg}}{t},$$

and $$\frac{i_r}{i_g} = 1000,$$

and $t_{1/2}=0.1$, then Equation 5 for measure glass impedance Rm can be further approximated as:

$$R_m = R_g - \frac{100}{C_{sg}} \quad \text{Eq. 6}$$

where $R_g$ is the resistance of the pH measuring glass and $C_{sg}$ is the double layer capacitance of solution ground 110. Since the actual glass impedance is on the order of 100 Mohm, optimally, the $C_{sg}$ should be equal or larger than 10 $\mu F$. However, since the above equation shows that the measured glass impedance $R_m$ will always be smaller than the real glass impedance, $R_g$, it is clear that external solution ground 110 introduces error in measuring glass bulb impedance $R_g$ during diagnostics.

Figure 5:
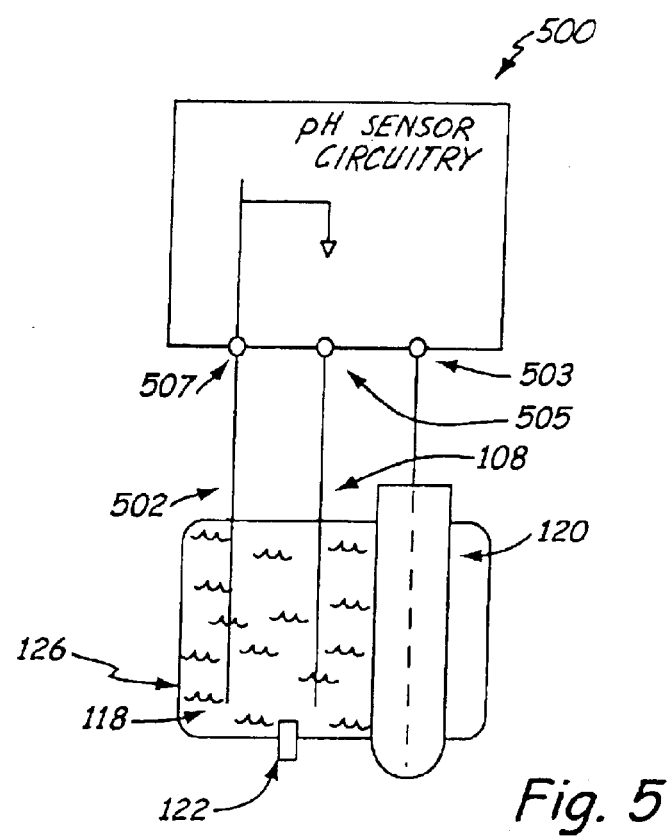
FIG. 5 illustrates a diagrammatic view of a pH sensor having an internal solution ground.

In FIG. 5, internal solution ground 502 comprises a conductor made of an electrode material such as Ag/AgCl or platinum Pt electrically connected to circuit common at terminal 507 and in contact with reference solution 118. However, other metal or non-metal electrode materials can be used. Internal solution ground 502 shares liquid junction 122 as does reference electrode 108.

Advantages of an Internal Solution Ground

FIG. 5 illustrates improved pH sensor assembly 500 having internal solution 502 ground positioned within sensor container 126 in contact with reference solution 118. Theoretically, internal solution ground 502 increases the accuracy of the pH sensor 500 in both pH measurements and with diagnostics, especially glass bulb impedance. Since internal solution ground 502 is in contact with the reference solution 118 rather than liquid sample (not shown), a much more stable potential difference $E_{sg}$ can be maintained by the internal solution ground 502.

Experimentally, a third electrode 502 made of Ag/AgCl, the same material as reference electrode 108, was positioned within sensor container 126 behind liquid junction 122. Because the third electrode 502 was behind the liquid junction 122, this third electrode 502 has been described as internal solution ground 502. Internal solution ground 502 was found to have a very stable potential $E_{sg}$ compared with prior art sensor 100 having metal external solution ground 110 as illustrated in FIG. 1.

Figure 6:
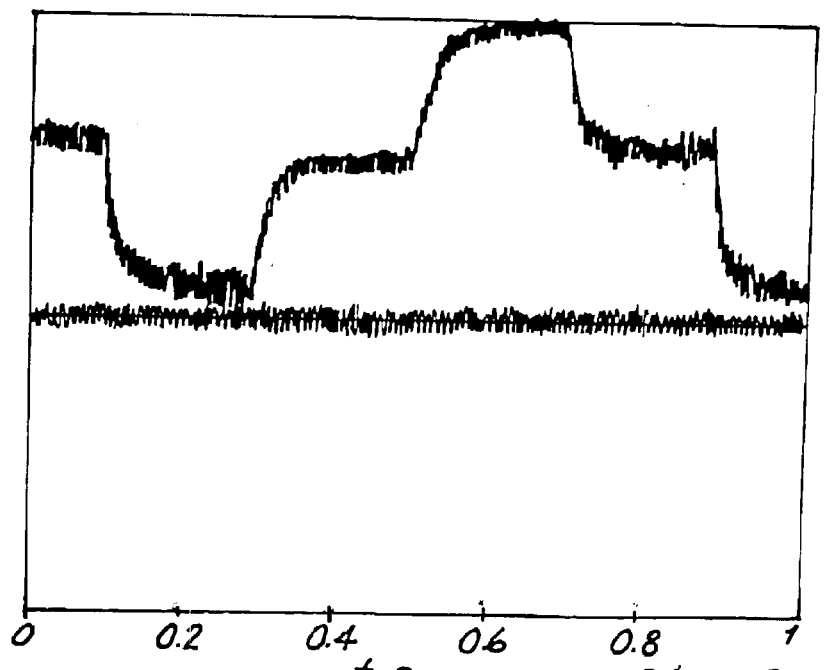
FIG. 6 shows oscilloscope results of voltages across pH electrode and reference electrode of pH sensor having internal solution ground having desirable limited ramping.

FIG. 6 shows oscilloscope test results for the positive and negative current junction test as in FIG. 4 substituting sensor 500 with Ag/AgCl internal solution ground 502 instead of platinum external solution ground 110. As can be seen in FIG. 6, sensor 500 with internal solution ground 502 did not have as much ramping as sensor 100 results shown in FIG. 4. Less oscilloscope ramping is desirable because it indicates a more accurate pH sensor 500.

In addition to increased accuracy, an internal solution ground 502 is advantageous due to lower manufacturing costs compared to external solution ground 110. It is much easier to add an electrode 502 to reference solution 118 when compared with positioning and attaching a metal with a discrete surface area to the outside of the sensor housing or container 126 as is generally necessary for an external solution ground 110. Also, an internal solution ground 502 does not likely add an additional fault location as does external solution ground 110.

Ground Loop Problems

Figure 7:
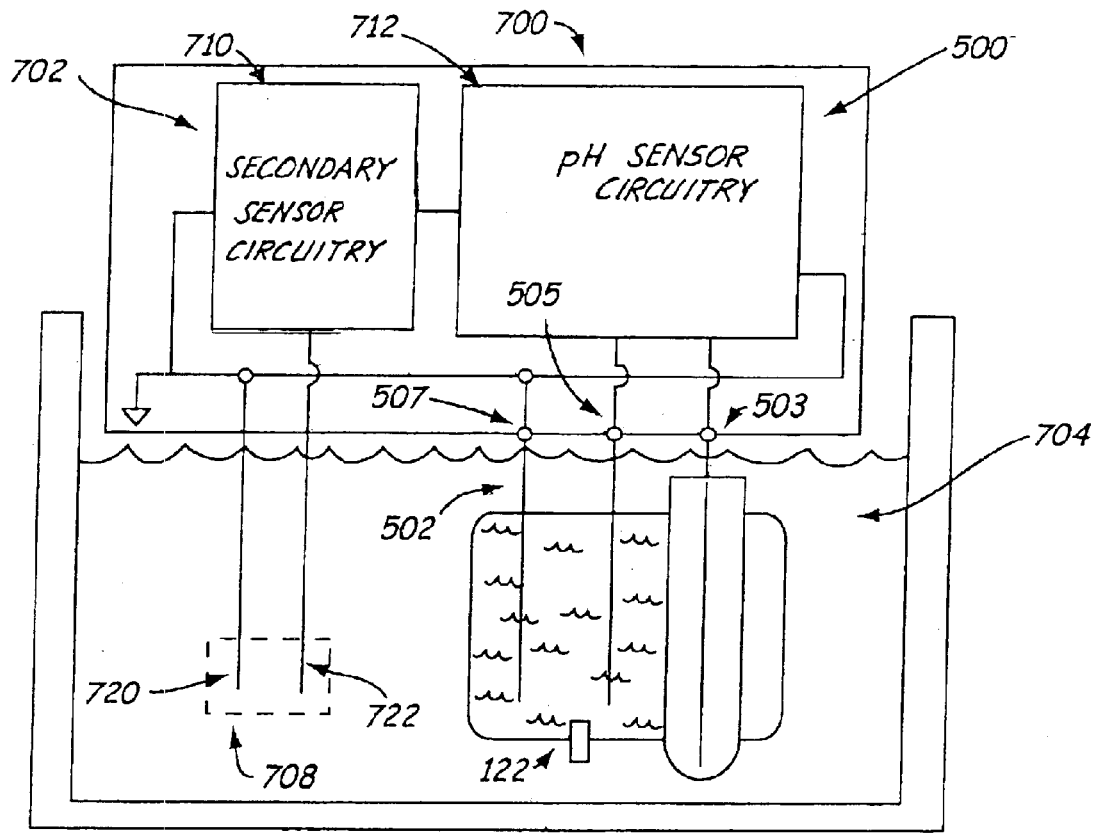
FIG. 7 illustrates a diagrammatic view of an instrument monitoring a pH sensor with internal solution ground and a secondary sensor in contact with liquid sample.

The trend in pH sensor design and instrumentation is to lower cost and increase flexibility by employing multi-sensing instrument 700, such as illustrated in FIG. 7, that can monitor pH sensor 500 and at least one secondary sensor 702 having non-isolated circuitry 710, 712 simultaneously. Non-isolation is due to use of a single power supply, not shown, to provide power for circuits 710, 712. Secondary sensor 702 can be another pH sensor, a conductivity sensor (as illustrated having electrodes 720 and 722), amperometric sensor. In this manner, a customer can purchase a single instrument 700 instead of multiple single-purpose instruments when necessary or desirable to measure more than one property of liquid sample 704. Circuitry 710 and 712 are well known and can take many forms.

During experimentation, pH sensor 500 illustrated in FIG. 5 having an internal solution ground 502 was found to be more accurate when used by itself. However, sensor 500 had accuracy problems when used with a secondary sensor 702. FIG. 7 illustrates pH sensor 500 of FIG. 5 with a secondary sensor 702 in liquid sample 704. Multi-sensing instrument 700 is designed to monitor both sensors 500, 702 simultaneously. Using the apparatus of FIG. 7, pH measurements of pH sensor 500 changed drastically when secondary sensor probe 708 was added to liquid sample 704. The drastic pH change was particularly apparent when secondary sensor 702 was a conductivity sensor but accuracy problems also arose when the secondary sensor was another pH sensor, amperometric sensor, conductivity sensor or other similar electrochemical sensors. It is noted that reference numeral 720 can indicate the grounded outer electrode of many conventional conductivity sensors.

Figure 8:
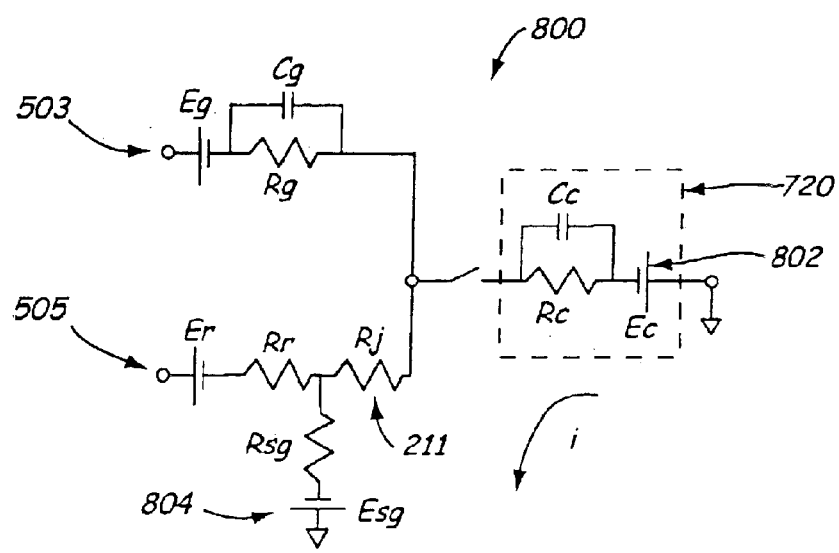
FIG. 8 illustrates a partial equivalent circuit of the instrument of FIG. 7.

FIG. 8 is a partial equivalent circuit 800 of the FIG. 7 assembly and helps illustrate the reason for the drastic change in pH of sensor 500 in FIG. 7. A ground loop i arises from potential difference $E_c-E_{sg}$ between reference electrode 720 shown generally as potential $E_c$ 802 and internal solution ground shown generally at potential $E_{sg}$ 804 in FIG. 8.

The circuits of pH sensor 500 and at least one secondary sensor 702 are not electrically isolated within multi-sensing instrument 700. Therefore, potential difference $E_c-E_{sg}$ can cause ground loop current i to flow between reference electrode 720 of secondary sensor 702 to solution ground 502. According to Ohm's Law, a potential drop of $iR_J$ is thus established at liquid junction 122 having resistance $R_J$ illustrated as 211 in FIG. 8.

The result of ground loop i is potential difference $V_g-V_r$ discussed above, measured at terminals 503, 505, respectively, no longer corresponds with the pH signal $E_g-E_r$ as before. Instead the potential difference $V_g-V_r$ is equal to $E_g-E_r+iR_J$ where $iR_J$ is the voltage drop over the liquid junction 122 caused by the ground loop current i.

Multi-Sensing Instrument

Figure 9:
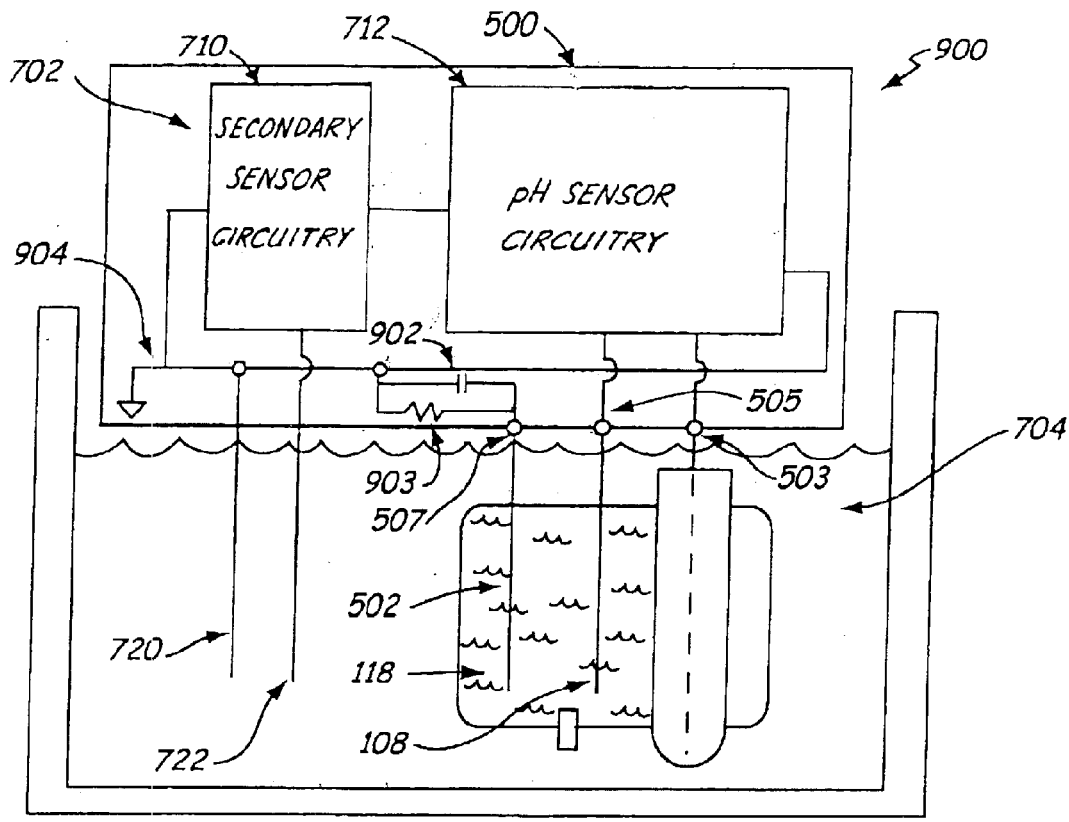
FIG. 9 illustrates a diagrammatic view of a multi-sensing instrument having a pH sensor with internal solution ground, a secondary sensor in contact with liquid sample and a capacitor connected between common and the internal solution ground.

It has been discovered as another aspect of the present invention that multi-sensing instrument 900, such as that illustrated in FIG. 9, having capacitor 902 connected between common 904 and internal solution ground 502 provides DC or low frequency isolation between solution ground 502 and common 904 thereby leading to stable pH measurements in pH sensor 500 as monitored by instrument 900. Capacitor 902 inhibits DC or low frequency ground loop current i between the electrodes of sensors 500 and 702.

In accordance with the discussion of Equation 6 above, capacitor 902 should be approximately 10 $\mu$F or greater; however, this value of capacitance may vary due to $i_r$, $i_g$, and $t_{1/2}$ employed, as indicated in equation (5). It is noted that capacitor 902 can also help inhibit ground loop current from stray voltage leaking into reference solution 118 from internal solution ground 502. Stray voltage leaking into reference solution 118 is generally associated with other ground loops and hence errors in pH measurement and degradation and shortened life of reference electrode 108.

Although illustrated where capacitor 902 is operably connected to electrode 502, in an alternative embodiment, capacitor 902 can be operably connected to provide isolation of reference electrode 720 of sensor circuitry 710.

Figure 10:
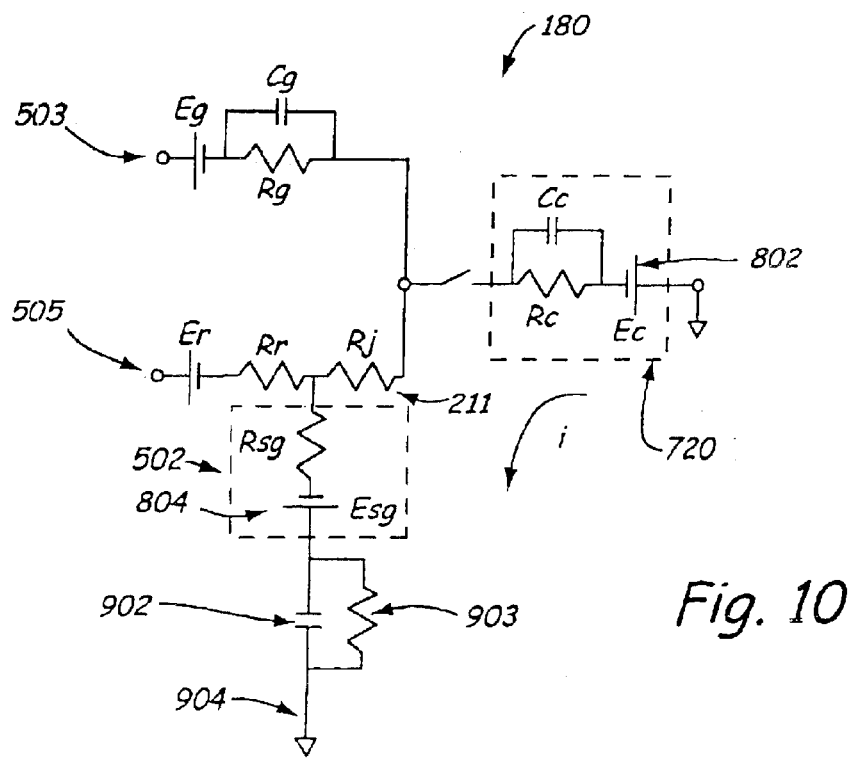
FIG. 10 illustrates a partial equivalent circuit of the instrument of FIG. 9.

As illustrated, partial equivalent circuit 180 in FIG. 10, capacitor 902 is placed between circuit common 904 and internal solution ground 502. The potential difference $E_g-E_r$ associated with pH at terminals 503 and 505 become stable even if secondary sensor 702 is a conductivity sensor. Also illustrated in FIGS. 9 and 10 is optional resistor 903 which has a suitably high resistance value electrically connected in parallel across capacitor 902 to discharge any accumulated charge on capacitor 902.

Figure 11:
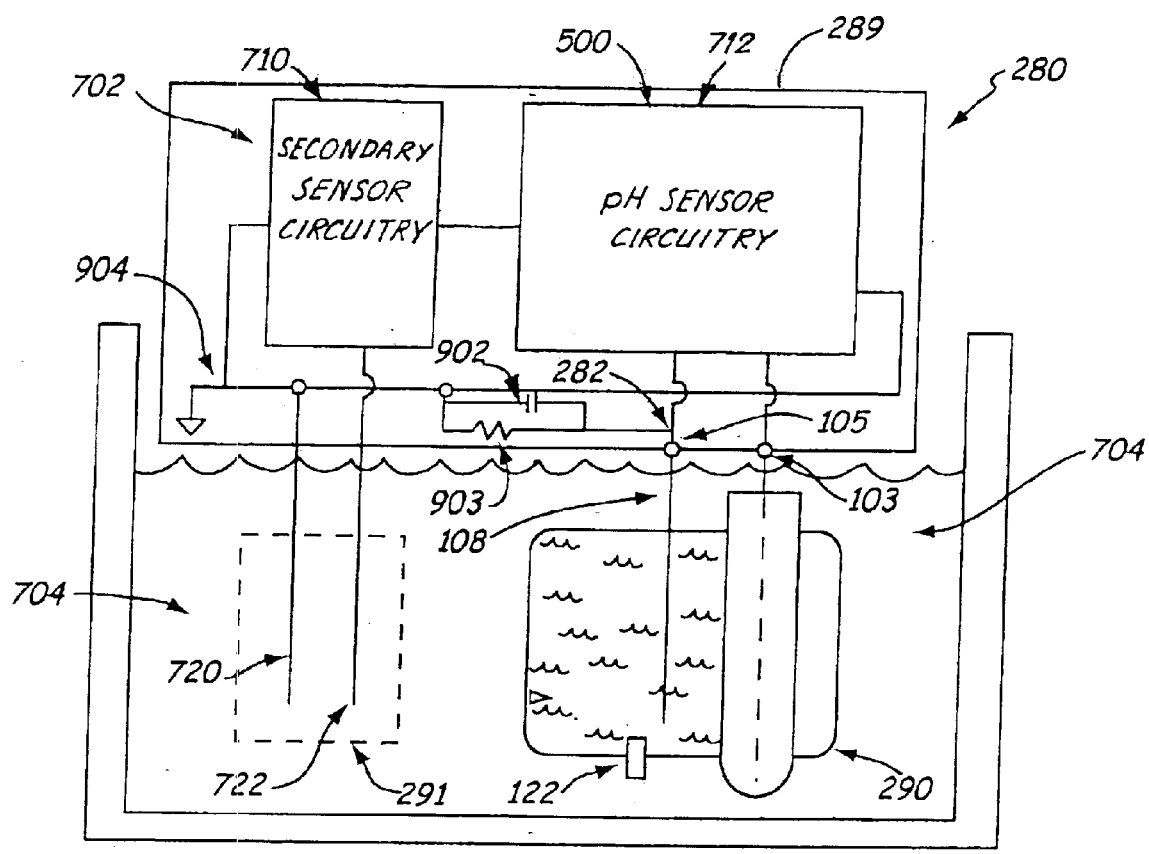
FIG. 11 illustrates a diagrammatic view of the instrument of FIG. 9 alternately omitting the internal solution ground and connecting the capacitor from common to the reference electrode.

In a further embodiment, FIG. 11 illustrates multi-sensing instrument 280 having pH sensor 500 with circuitry 712 and at least one secondary sensor 702 with circuitry 710. Capacitor 902 is electrically connected between circuit common 904 and reference electrode 108 at node 282. Ground loop current has also been generally found to be problematic whenever two or more sensors 500, 702 each having reference electrodes in operable contact with liquid sample 704. This ground loop i through reference electrodes 108, 720 or 722 is somewhat similar to the ground loop in pH sensor 500 having internal solution ground 502 and secondary sensor 702 illustrated in FIG. 7.

Generally, when there are two sensors each having a reference electrode operably contacting a liquid sample, a potential difference develops between the reference electrodes. The potential difference $V_g-V_r$ measured at terminal 103 and terminal 105 will no longer indicate potential difference $E_g-E_r$ which is the pure signal for pH measurement discussed previously.

Figure 12:
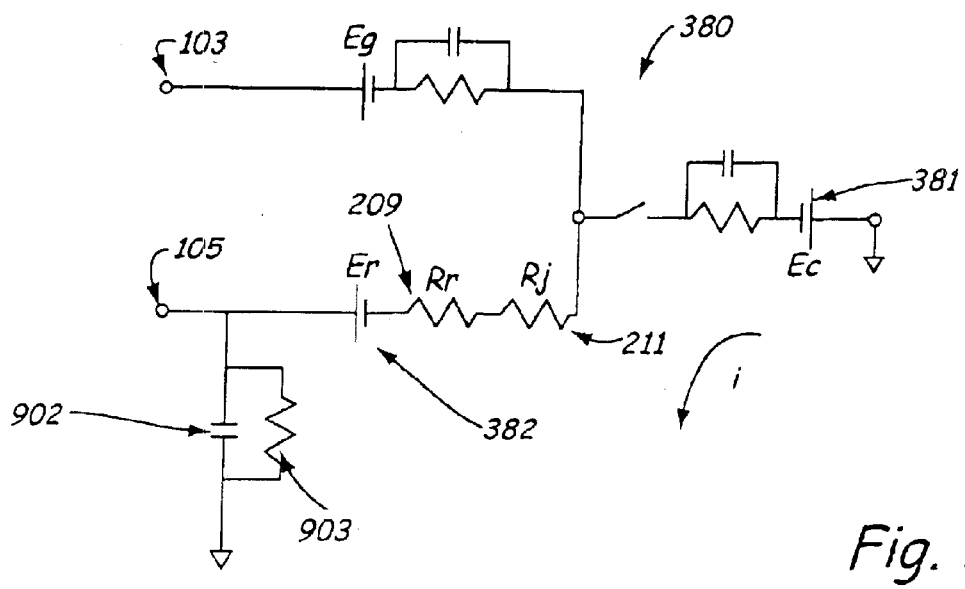
FIG. 12 illustrates a partial equivalent circuit of the instrument of FIG. 11.

Instead, as illustrated in FIG. 12, partial equivalent circuit 380 potential difference $V_g-V_r$ at terminals 103 and 105 would be $E_g-E_r+i(R_j+R_r)$ where $R_r$ is the resistance of the reference electrode 108 shown as 209 and $R_j$ is the resistance of liquid junction 122 shown as reference numeral 211. In this case, capacitor 902 is connected to one of the reference electrodes and will inhibit ground loop current i. One advantage of using capacitor 902 in this manner is that modifications of existing pH sensors are not needed.

Capacitor 902 can be placed within the circuitry of multi-sensing instrument 280, i.e. within the housing 289 thereof, monitoring remote sensor probes 290, 291. Probes 290, 291 having the sensing electrodes can be electrically connected to instrument 280 over relatively long distances. In cases of monitoring remote probes 290, 291, it can be cost effective to eliminate internal solution ground 502 because it is a third wire that requires installation and provides a potential fault location. It should be noted that capacitor 902 can be used where intrinsically safe equipment is desirable.

Figure 13:
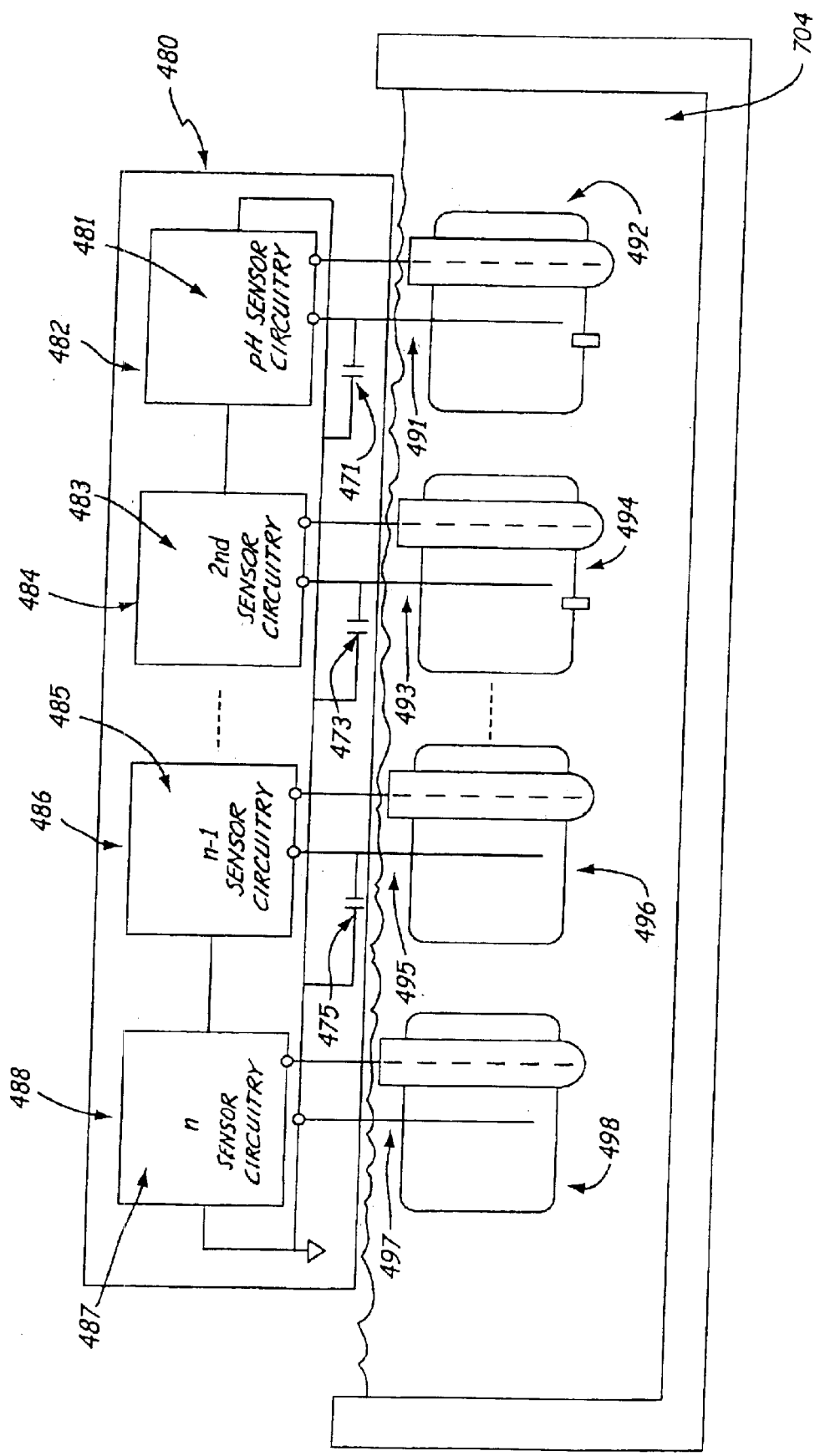
FIG. 13 illustrates a diagrammatic view of a multi-sensing instrument.

In a further embodiment shown in FIG. 13, multi-sensing instrument 480 monitors pH sensor 482 having circuitry 481 and probe 492 in liquid sample 704 and a plurality of secondary sensors 484, 486, 488, each having probes 494, 496, 498 adapted to be placed in liquid sample 704. Circuitries 481, 483, 485, 487 of all sensors 482, 484, 486, 488 are electrically non-isolated within multi-sensing instrument 480. Ground loops can develop between any pair of reference electrodes 491, 493, 495, 497 since all are in operable contact with liquid sample 704.

If the total number of sensors including pH sensor 482 is equal to n, as illustrated in FIG. 13, the total number of capacitors 471, 473, 475 can be equal to the number of secondary sensors or the total numbers of sensors minus one to adequately inhibit all ground currents.

Although the present invention has been described with reference to preferred embodiments, workers skilled in the art will recognize that changes may be made in form and detail without departing from the spirit and scope of the invention.

What is claimed is:

1. A pH sensor assembly comprising:
   a pH electrode;
   a reference electrode assembly comprising a container containing an electrolyte solution in contact with a liquid junction extending to an outside surface of the container and a reference electrode disposed in the container and in contact with the electrolyte solution; and
   an internal solution ground comprising a conductor disposed within the container, in contact with the electrolyte solution, and electrically connected to a circuit common; and
   a capacitor electrically connected between the conductor and the circuit common.

2. The pH sensor assembly of claim 1, and further comprising circuitry having a first terminal electrically connected to the reference electrode and a second terminal electrically connected to the pH electrode.

3. The pH sensor assembly of claim 2, wherein the capacitor is directly electrically connected to at least one of the circuit common and the conductor.

4. A pH sensor assembly comprising:
   a pH electrode;
   a reference electrode assembly comprising a container containing an electrolyte solution in contact with a liquid junction extending to an outside surface of the container and a reference electrode disposed in the container and in contact with the electrolyte solution; and
   an internal solution ground comprising a conductor disposed within the container, in contact with the electrolyte solution, and electrically connected to the circuit common;
   circuitry having a first terminal electrically connected to the reference electrode and a second terminal electrically connected to the pH electrode;
   a capacitor electrically connected to the conductor and electrically connected to a common of the circuitry; and
   a resister electrically connected in parallel across the capacitor.

5. A multi-sensing instrument having a circuit common, the multi-sensing instrument comprising:
   a pH sensor assembly comprising:
      a pH electrode;
      a reference electrode assembly comprising a container containing an electrolytic reference solution in contact with a liquid junction extending to an outside surface of the container, the container adapted to be placed in a liquid to be sensed, and a first reference electrode disposed in the container and in contact with the reference solution; and
      a pH sensing circuit having a first terminal connected to the reference electrode and a second terminal electrically connected to the pH electrode;
   a second sensor, assembly comprising:
      a second reference electrode adapted to be operably coupled to the liquid to be sensed;
      a second sensing circuit having a terminal electrically connected to the second reference electrode, the first and second sensing circuitry electrically connected to the circuit common; and
   a capacitor electrically connected between the circuit common and one of the first and second reference electrodes to inhibit ground loop currents.

6. The multi-sensing instrument of claim 5, wherein the second sensing circuit is a pH sensing circuit.

7. The multi-sensing instrument of claim 5, wherein the second sensing circuit is a conductivity circuit.

8. The multi-sensing instrument of claim 5, wherein the second sensing circuit is an amperometric sensing circuit.

9. The multi-sensing instrument of claim 5, and further comprising one and only one power supply adapted to provide power to the pH sensing circuit and the second sensing circuit.

10. The multi-sensing instrument of claim 5, and further comprising:
    at least one additional secondary sensor assembly comprising a third reference electrode adapted to be operably coupled to the liquid to be sensed and a third sensing circuit having a terminal electrically connected to the third reference electrode, the third sensing circuitry electrically connected to the circuit common; and
    a second capacitor electrically connected between the circuit common and the third reference electrode.

11. A multi-sensing instrument having a circuit common, the multi-sensing instrument comprising:
    a pH sensor assembly comprising:
       a pH electrode;
       a reference electrode assembly comprising a container containing an electrolytic reference solution in contact with a liquid junction extending to an outside surface of the container, the container adapted to be placed in a liquid to be sensed, and a first reference electrode disposed in the container and in contact with the reference solution; and
       a pH sensing circuit having a first terminal connected to the reference electrode and a second terminal electrically connected to pH electrode;
    a second sensor assembly comprising:
       a second reference electrode adapted to be operably coupled to the liquid to be sensed;
       a second sensing circuit having a terminal electrically connected to the second reference electrode, the first and second sensing circuitry electrically connected to the circuit common;
    a capacitor electrically connected between the circuit common and one of the first and second reference electrodes; and
    a resistor electrically connected in parallel across the capacitor.

12. The multi-sensing instrument of claim 11, and further comprising one and only one power supply adapted to provide power to the pH sensing circuit and the second sensing circuit.

* * * * *